US00PP12152P2

(12) United States Plant Patent
Vlielander

(10) Patent No.: US PP12,152 P2
(45) Date of Patent: Oct. 16, 2001

(54) KALANCHOE PLANT NAMED 'LICAN'

(75) Inventor: Ike Vlielander, Maasland (NL)

(73) Assignee: Fides Goldstock Breeding B.V., Maasland (NL)

( * ) Notice: Subject to any disclaimer, the term of this patent is extended or adjusted under 35 U.S.C. 154(b) by 0 days.

(21) Appl. No.: 09/778,207

(22) Filed: Feb. 8, 2001

(51) Int. Cl.[7] ..... A01H 5/00

(52) U.S. Cl. ..... Plt./339

(58) Field of Search ..... Plt./339, 337, 347

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Kalanchoe plant named 'Lican', characterized by its numerous, large, and intense purple-colored flowers; upright and uniform plant habit; freely branching growth habit; dark green and glossy leaves; early flowering; and excellent postproduction longevity.

1 Drawing Sheet

BACKGROUND OF THE INVENTION

The present invention relates to a new and distinct cultivar of Kalanchoe plant, botanically known as *Kalanchoe blossfeldiana*, and hereinafter referred to by the name 'Lican'.

The new Kalanchoe is a product of a planned breeding program conducted by the Inventor in De Lier, The Netherlands. The objective of the breeding program was to create new free-branching Kalanchoe cultivars with compact plant habit, numerous flowers, and attractive foliage and flower coloration.

The new Kalanchoe originated from a cross made by the Inventor in 1996 of the *Kalanchoe blossfeldiana* cultivar Iztac, disclosed in U.S. Plant Pat. No. 10,455, as the female, or seed, parent with the *Kalanchoe blossfeldiana* cultivar Isabella, disclosed in U.S. Plant Pat. No. 9,427, as the male, or pollen, parent. The cultivar Lican was discovered and selected by the Inventor as a flowering plant within the progeny of the stated cross in a controlled environment in De Lier, The Netherlands.

Asexual reproduction of the new Kalanchoe by terminal cuttings taken at De Lier, The Netherlands, since 1996 has shown that the unique features of this new Kalanchoe are stable and reproduced true to type in successive generations.

BRIEF SUMMARY OF THE INVENTION

The cultivar Lican has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Lican'. These characteristics in combination distinguish 'Lican' as a new and distinct cultivar:

1. Numerous, large, and intense purple-colored flowers.
2. Upright and uniform plant habit.
3. Freely branching growth habit.
4. Dark green and glossy leaves.
5. Early flowering.
6. Excellent postproduction longevity.

Plants of the new Kalanchoe can be compared to plants of the female parent, the cultivar Iztac. In side-by-side comparisons conducted by the Inventor in De Lier, The Netherlands, plants of the new Kalanchoe differ from plants of the cultivar Iztac in the following characteristics:

1. Plants of the new Kalanchoe are more compact than plants of the cultivar Iztac.
2. Plants of the new Kalanchoe have smaller leaves than plants of the cultivar Iztac.
3. Flowers of plants of the new Kalanchoe are intense purple in color whereas flowers of plants of the cultivar Iztac are dark pink in color.

Plants of the new Kalanchoe can be compared to plants of the male parent, the cultivar Isabella. In side-by-side comparisons conducted by the Inventor in De Lier, The Netherlands, plants of the new Kalanchoe differ from plants of the cultivar Isabella in the following characteristics:

1. Plants of the new Kalanchoe are more compact than plants of the cultivar Isabella.
2. Plants of the new Kalanchoe are more freely branching than plants of the cultivar Isabella.
3. Leaves of the new Kalanchoe are not as twisting as leaves of the cultivar Isabella.
4. Flower color of plants of the new Kalanchoe is darker and more intense purple than flower color of plants of the cultivar Isabella.

Plants of the new Kalanchoe can also be compared to plants of the cultivar Timor, not patented. In side-by-side comparisons conducted by the Inventor in De Lier, The Netherlands, plants of the new Kalanchoe differ from plants of the cultivar Timor in the following characteristics:

1. Plants of the new Kalanchoe are more freely branching than plants of the cultivar Timor.
2. Inflorescence form of plants of the new Kalanchoe is not as open as inflorescence form of plants of the cultivar Timor.
3. Plants of the new Kalanchoe flower earlier than plants of the cultivar Timor.
4. Flower color of plants of the new Kalanchoe is darker and more intense purple than flower color of plants of the cultivar Timor.

BRIEF DESCRIPTION OF THE PHOTOGRAPH

The accompanying colored photograph illustrates the overall appearance of the new Kalanchoe, showing the colors as true as it is reasonably possible to obtain in colored reproductions of this type. Colors in the photograph may differ slightly from the color values cited in the detailed botanical description which accurately describe the colors of the new Kalanchoe. The photograph comprises a side perspective view of a typical potted plant of 'Lican'.

DETAILED BOTANICAL DESCRIPTION

In the following description, color references are made to The Royal Horticultural Society Colour Chart except where general terms of ordinary dictionary significance are used. Unpinched plants used for the photograph and for the description were grown during the autumn in De Lier, The Netherlands, in a glass-covered greenhouse. During the production of the plants, the following measurements were recorded: day temperatures about 19 to 26° C.; night temperatures about 20 to 21° C.; and light levels about 10,000 to 50,000 lux. Unrooted cuttings were directly stuck in 10-cm containers and received long day/short night conditions (more than 14 hours of light) for about 22 days; plants then received photoinductive short day/long night conditions (minimum 14 hours darkness) until flowering. Plants were about 14 weeks old from an unrooted cutting when the photograph and the description were taken.

Botanical classification: *Kalanchoe blossfeldiana* cultivar Lican.

Parentage:

*Female or seed parent.*—*Kalanchoe blossfeldiana* cultivar Iztac, disclosed in U.S. Plant Pat. No. 10,455.

*Male, or pollen, parent.*—*Kalanchoe blossfeldiana* cultivar Isabella, disclosed in U.S. Plant Pat. No. 9,427.

Propagation:

*Type cutting.*—Teminal cuttings.

*Time to initiate roots.*—Summer: About 10 days at 21° C. Winter: About 14 days at 21° C.

*Time to produce a rooted cutting.*—Summer: About 21 days at 21° C. Winter: About 28 days at 21° C.

*Root description.*—Numerous, fine, fibrous, and well-branched.

Plant description:

*Form.*—Upright and uniform plant habit, relatively compact, with numerous compound cymes; very freely flowering. Inverted triangle with rounded crown; actual plant shape will depend on whether or not plants are pinched (apical terminals removed). Appropriate for 10 to 15-cm containers.

*Crop time.*—About 11 to 14 weeks: 3 to 4 weeks under long day/short night conditions followed by 8 to 10 weeks of short day/long night conditions. Moderate growth rate.

*Plant height at flowering.*—About 20 cm.

*Plant diameter at flowering.*—About 19 cm.

*Branching habit.*—Freely branching; typically 7 to 8 lateral branches develop per plant. Pinching (removal of terminal apex) is not required but will enhance lateral branch development.

*Lateral branch description.*—Length: About 13 to 19 cm. Diameter: About 3 to 6 cm. Internode length: About 2 to 3 cm. Aspect: Erect. Strength: Moderately strong. Texture: Smooth, glabrous. Color: 147A.

*Foliage description.*—Leaves simple, opposite, generally symmetrical. Quantity per plant: About 8 to 13 mature leaves and 14 to 22 generative leaves. Length: About 12 cm. Width: About 9 cm. Aspect: Slight tendency to twist; concave. Shape: Ovate to elliptic. Apex: Acute to obtuse. Base: Acute. Margin: Crenate. Texture: Leathery, glabrous and succulent. Color: Young and mature foliage, upper surface: 147A; venation, 147A to 147B. Young and mature foliage, lower surface: 147B; venation, 147B. Petiole length: About 1.5 cm. Petiole diameter: About 4 by 8 mm. Petiole color: Upper surface, 147A to 147B; lower surface, 147B.

Flower description:

*Flower type and habit.*—Single flowers arranged in compound dichasial cymes that arise from leaf axils. Freely flowering; more than 25 open flowers per lateral branch and more than 150 open flowers per plant. Flowering continuously for at least 7 weeks. Flowers persistent. Flowers not fragrant.

*Natural flowering season.*—Plants of the new Kalanchoe initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about 8 to 10 weeks are required. Actual time to flower is primarily dependent upon temperature and light intensity.

*Post-production longevity.*—Excellent post-production longevity; plants maintain good foliage and flower substance for about 55 days under interior environmental conditions. Individual flowers last about 22 days on the plant.

*Flower diameter.*—About 1.7 cm.

*Flower height.*—About 1.3 cm.

*Flower buds.*—Shape: Initially oblong, becoming tubular ovoid with development. Length: About 1.3 cm. Width: About 3 mm. Color: Initially, 138C, then 63D with development.

*Petals.*—Quantity: Four fused at base. Length: About 8 mm. Width: About 6 mm. Aspect: Flat to slightly upright. Shape: Ovate. Apex: Acute. Margin: Entire. Texture: Glabrous, smooth and satiny. Color: When opening and fully opened, upper surface: 74A; flower color does not fade with subsequent development. When opening and fully opened, lower surface: 70D.

*Sepals.*—Quantity: Four fused at base. Length: About 7 mm. Width: About 3 mm. Aspect: Erect. Shape: Oblong. Apex: Acute. Margin: Entire. Texture: Glabrous, smooth. Color, both surfaces: 138D.

*Peduncles.*—Length: About 8 mm. Diameter: About 1 mm. Aspect: Erect. Strength: Strong, flexible. Texture: Smooth, leathery. Color: 138B.

*Reproductive organs.*—Stamens: Stamen number: Eight per flower. Anther shape: Flat, elliptic. Anther size: About 0.3 mm. Anther color: Close to 150D. Pollen amount: Scarce. Pollen color: 12A. Pistils: Pistil number: Four per flower. Style length: About 1 cm. Style color: 138D. Stigma shape: Flat, rounded. Stigma color: 8D. Ovary color: 138D.

*Seed.*—Seed production has not been observed.

Disease resistance: Plants of the new Kalanchoe have not been observed to be resistant to pathogens common to Kalanchoes.

Temperature tolerance: Plants of the new Kalanchoe have been observed to tolerate low temperatures of 12° C. and high temperatures of 35° C.

Garden performance: Plants of the new Kalanchoe perform have been observed to perform well in the garden and are tolerant to rain and wind.

It is claimed:

1. A new and distinct cultivar of Kalanchoe plant named 'Lican', as illustrated and described.

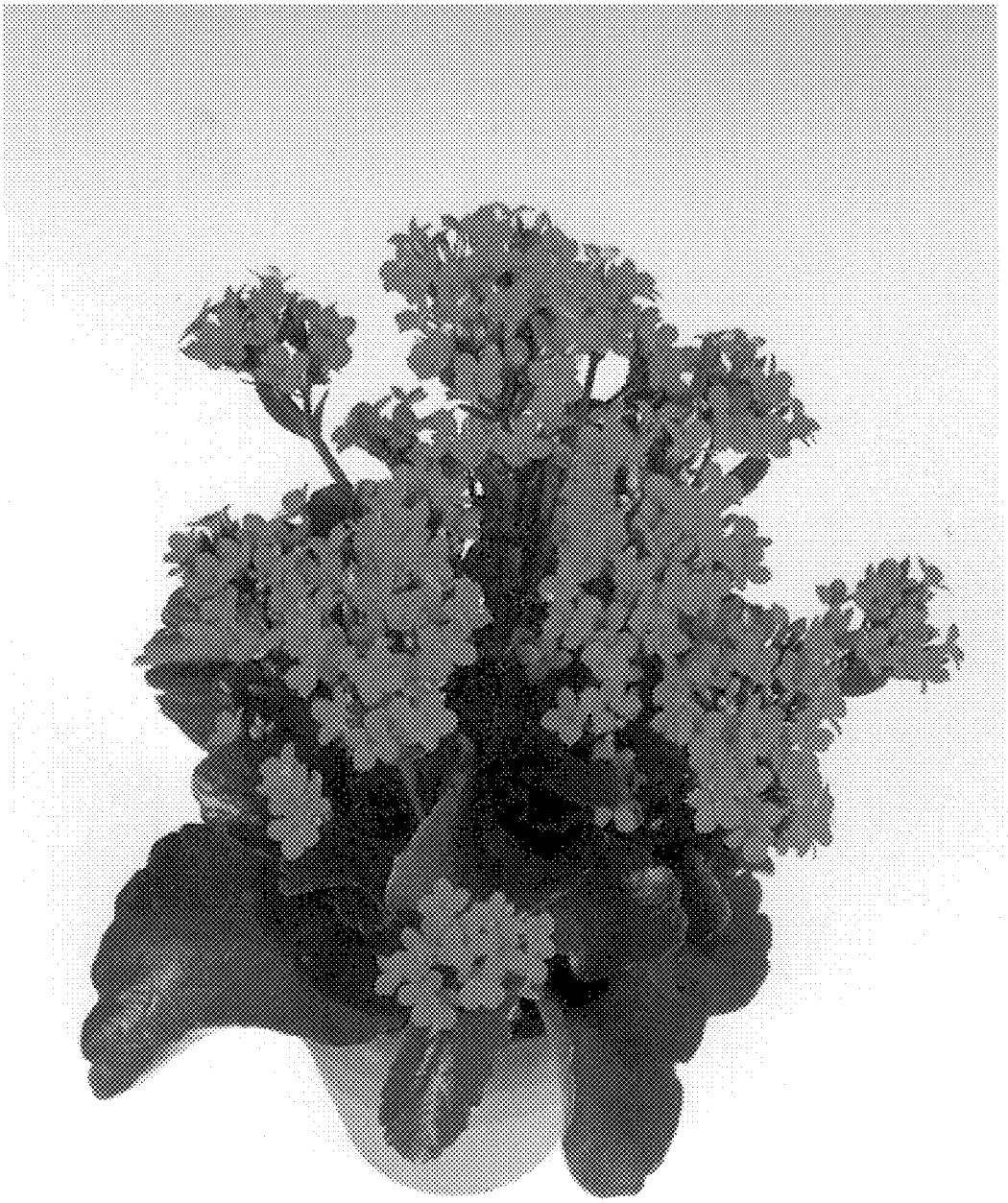

* * * * *